United States Patent [19]

Dormer et al.

[11] 4,352,960
[45] Oct. 5, 1982

[54] MAGNETIC TRANSCUTANEOUS MOUNT FOR EXTERNAL DEVICE OF AN ASSOCIATED IMPLANT

[75] Inventors: Kenneth J. Dormer, Edmond; Gordon L. Richard, Minco, both of Okla.

[73] Assignee: Baptist Medical Center of Oklahoma, Inc., Oklahoma City, Okla.

[21] Appl. No.: 192,480

[22] Filed: Sep. 30, 1980

[51] Int. Cl.³ ........................... A61F 1/00; A61F 11/00
[52] U.S. Cl. .............................................. 179/107 BC
[58] Field of Search ................... 179/107 BC; 128/654

[56] References Cited

U.S. PATENT DOCUMENTS

| | | | |
|---|---|---|---|
| 3,061,689 | 10/1962 | McCarrell et al. | 179/107 |
| 3,346,704 | 10/1967 | Mahoney | 179/107 |
| 3,557,775 | 1/1971 | Mahoney | 179/107 |
| 3,712,962 | 1/1973 | Epley | 179/107 |
| 3,764,748 | 10/1973 | Branch et al. | 179/107 |
| 3,870,832 | 3/1975 | Fredrickson | 179/107 |

Primary Examiner—George G. Stellar
Attorney, Agent, or Firm—E. Harrison Gilbert, III

[57] ABSTRACT

Disclosed is a transcutaneous coupling apparatus comprising a first member subcutaneously positioned in a user of the invention and also comprising a second member positioned supercutaneously, or outside the skin of the user. Rare-earth magnets are associated with the first and second members to magnetically secure the second member with the first member without significantly adversely affecting the user's skin intervening between the first and second members.

21 Claims, 5 Drawing Figures

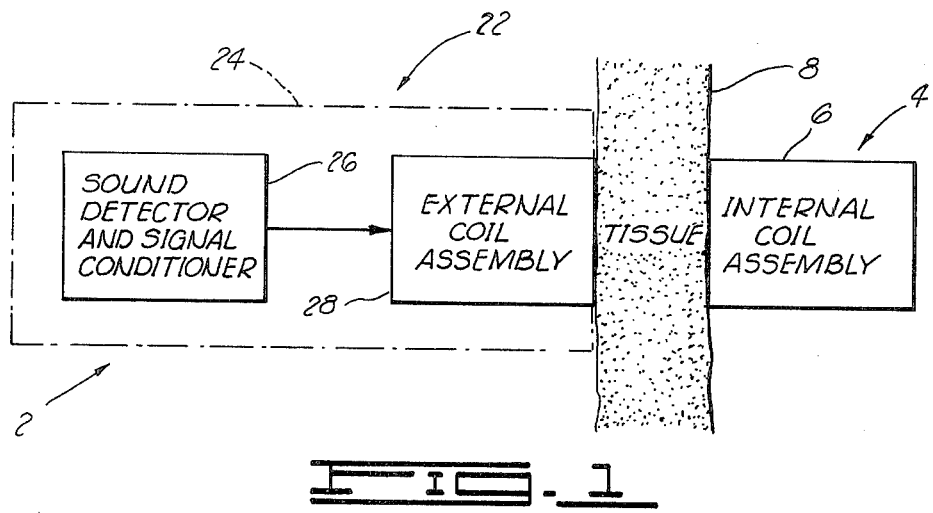
FIG. 1
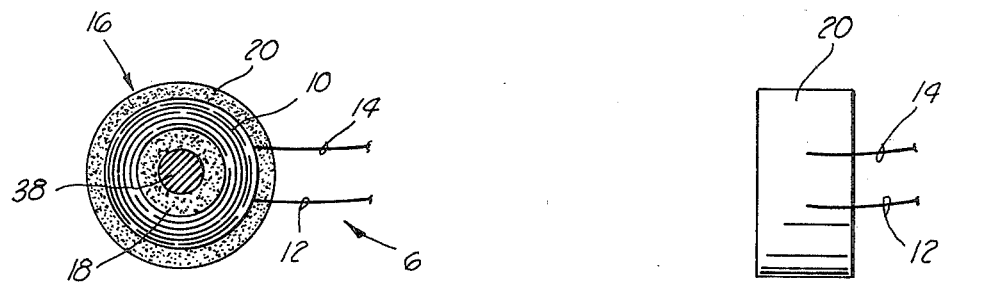
FIG. 2
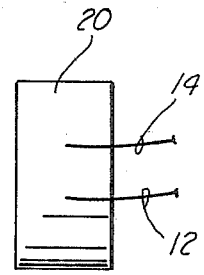
FIG. 3
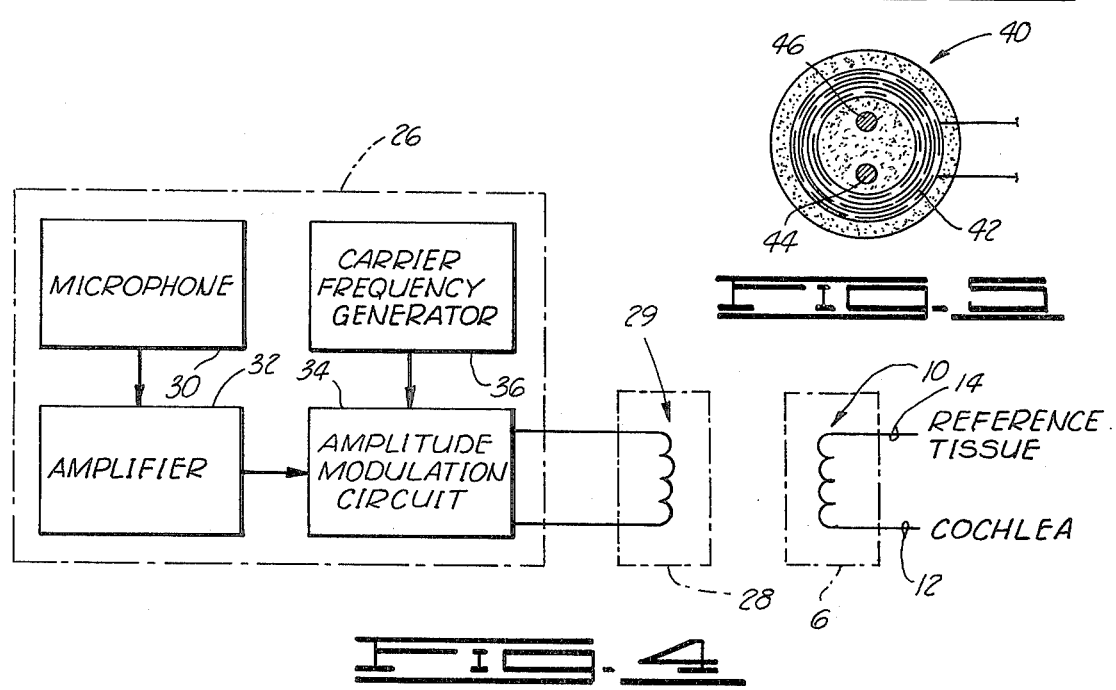
FIG. 4
FIG. 5

MAGNETIC TRANSCUTANEOUS MOUNT FOR EXTERNAL DEVICE OF AN ASSOCIATED IMPLANT

BACKGROUND OF THE INVENTION

This invention relates generally to apparatus for coupling a member implanted in a body with a member located outside the body. More particularly, but not by way of limitation, the invention relates to a bio-electronic signal coupling device (such as a hearing aid having a cochlear implant unit and a sound receiving unit) utilizing rare-earth magnets to properly align and secure an external member (such as the sound receiving unit) with an internal member (such as the cochlear implant unit).

In the medical implantable electronic prosthesis field it is necessary to maintain proper alignment between units implanted within the body and units associated therewith but located externally of the body. Specifically, in medical prostheses involving electrical signal transfers, such as hearing aids, it is critical to maintain a proper alignment between the implanted and external units to insure effective signal transfer.

For example, a hearing aid known as an auditory neural prosthesis is used to electrically stimulate a user's auditory nerve directly or within the cochlea thereby to enable recognition of environmental sounds and to improve lip-reading skills. Such a prosthesis includes an internal, subcutaneously located signal receiving unit implanted in the user so that an electrical signal can be conducted to a cochlea of the user. The prosthesis also includes an external sound detecting and transmitting unit located outside the skin of the user.

For the sound detecting and transmitting unit to effectively transmit to the receiving unit electrical signals corresponding to the detected sounds, the sound detecting and transmitting unit must be maintained in proper alignment with the receiving unit. Presently proposed or used devices attempt to maintain alignment by utilizing eyeglass frames specially constructed to carry the sound detecting and transmitting unit. This frame structure has the shortcoming of permitting misalignment between the external and internal units because the eyeglass frames can slip and otherwise become easily moved. Such misalignment decreases, if not totally eliminates, the amplitude of the coupled signal received by the receiving unit. This decrease or loss of signal results in decreased or lost cochlea stimulation which causes frustration in the user of the apparatus because he or she has to continually readjust the eyeglass frames to maintain the apparatus operative. This misalignment also hampers the training, evaluation and use of the prosthesis user.

If the eyeglass frame structure were used with multi-channel auditory neural prostheses which are being developed to provide frequency coding of detected sounds, the reliability of such multi-channel devices would be greatly decreased because accurate alignment is critical to insure that each of the plurality of signals transmitted by the transmitter means in the multi-channel transmitter unit is received by the proper receiver means in the implanted multi-channel receiving unit.

Although proper alignment must be maintained in medical apparatus having units located both beneath the surface of the skin and above the skin, it is desirable that there be no mechanical connection which extends through the skin of the user between the internal and external units. Although no mechanical connection, which could rigidly maintain a predetermined distance between the internal and external units so that no compression of the intervening skin occurred, is wanted, neither is there desired a coupling device which adversely affects, such as by compression, the skin extending between the implanted unit and the external unit. Therefore, what is desired is an apparatus which secures the external unit with the internal unit without adversely affecting the intervening tissue.

Although there have been proposed and made medical apparatus having implantable units and external units which need to be coupled or held in alignment by some means, such as the aforementioned type of hearing aid using an eyeglass frame, we do not know of any such apparatus which discloses or suggests our invention as disclosed and claimed hereinbelow.

SUMMARY OF THE INVENTION

The present invention overcomes the above-noted and other shortcomings of the prior art by providing a novel and improved medical apparatus coupling device. This apparatus maintains in proper alignment or desired positional securement a unit which is disposed beneath the surface of the skin of a user and a unit located outside the surface of the user's skin. Furthermore, there is no mechanical connection extending through the user's skin to maintain this alignment. Additionally, this present invention has no known significantly adverse effect on the user's skin extending between the internally located unit and the externally positioned unit.

Broadly, the present invention provides a transcutaneous coupling apparatus comprising a first member positioned subcutaneously, a second member positioned supercutaneously (i.e., outside the skin), and magnet means for magnetically securing the second member to the first member.

The first member includes in preferred embodiments electronic means which can receive an electrical signal or transmit an electrical signal or perform both functions. Likewise, the second member includes in a first embodiment means for transmitting the electrical signal to the receiving first member or in another embodiment includes electronic means for receiving the electronic signal transmitted by the first member. Alternatively, the second member can include means for performing both receiving and transmitting functions.

When the first and second members specifically include receiving and transmitting means, respectively, the transcutaneous coupling apparatus is a bio-electronic signal coupling device for maintaining a desired positional relationship between the first and second members so that the proper transmitting and receiving between the members can occur. In such an embodiment the first member specifically includes a first electrically conductive coil having two ends, each of which is embedded in tissue of the user of the apparatus. The second member in such an embodiment includes a second electrically conductive coil and signal generating means, electrically connected to the second coil, for providing an electrical signal to the second coil so that the signal is transferred by electromagnetic induction transcutaneously to the first coil for electrically stimulating the tissue in which the ends of the first coil are embedded.

The magnet means generally includes a rare-earth element. More particularly, the magnet means includes a first rare-earth magnet associated with the first coil of an embodiment of the first member, and the magnet means also includes a second rare-earth magnet associated with the second coil of an embodiment of the second member, for magnetically coupling with the first rare-earth magnet so that the first and second coils are positioned to achieve electromagnetically inductive coupling. To maintain the first and second members in a predetermined relation, the magnet means further includes a third rare-earth magnet associated with the first coil and a fourth rare-earth magnet, associated with the second coil, for magnetically coupling with the third rare-earth magnet. To achieve the predetermined alignment, the third and fourth magnets have as their attractive polarities magnetic poles of opposite polarities to the attractive polarities of the first and second magnets so that each of the magnets on the first member will be attracted to only one of the magnets located on the second member.

From the foregoing it is a general object of the present invention to provide a novel and improved medical apparatus coupling device. Other and further objects, features and advantages of the present invention will be readily apparent to those skilled in the art when the following description of the preferred embodiments is read in conjunction with the accompanying drawings.

BRIEF DESCRIPTION OF THE DRAWINGS

FIG. 1 is a schematic illustration and block diagram of a preferred embodiment of the present invention.

FIG. 2 is a sectional side elevational view of a coil assembly of the preferred embodiment of the present invention.

FIG. 3 is an end elevational view of the coil assembly shown in FIG. 2.

FIG. 4 is a schematic and block diagram of the electronic elements of the preferred embodiment of the present invention.

FIG. 5 is a sectional side elevational view of a coil assembly of a second preferred embodiment of the present invention.

DETAILED DESCRIPTION OF PREFERRED EMBODIMENTS OF THE INVENTION

The medical apparatus coupling device of the present invention provides transcutaneous coupling of a subcutaneously located first member with a supercutaneously (i.e., outside the skin) positioned second member. To describe this invention, specific reference will be made to preferred embodiments of a bio-electronic signal coupling device which assists the hearing of a user of the device. The signal coupling device is particularly a hearing aid 2 schematically illustrated by the block diagram shown in FIG. 1.

The hearing aid 2 includes an internal first member 4 which is designated in FIG. 1 as an internal coil assembly 6. In the preferred embodiment the internal coil assembly 6 is a cochlear implant unit containing electronic receiver means for receiving a transmitted signal. However, it is to be noted that in other embodiments the internal coil assembly 6 can include means for transmitting a signal or means for both receiving and transmitting signals. Units other than signal receiving or transmitting ones can also comprise the first member.

The internal coil assembly 6 is subcutaneously located beneath a layer of tissue 8 which includes the epidermal and dermal layers of the skin of the user of the device when the device is the preferred embodiment hearing aid 2. FIGS. 2 and 4 disclose that the internal coil assembly 6 includes a first electrically conductive coil 10 of wire having two ends embedded in subcutaneous tissue. Specifically, as shown in FIG. 4 a first end or electrode 12 of the coil 10 is inserted in a cochlea of the user and a second end or electrode 14 is inserted in adjacent tissue as a reference electrode. In the preferred embodiment the first coil 10 comprises six hundred turns of 40 AWG copper wire. This wire is wound on a first support member 16 comprising a delrin bobbin 18 placed in a ceramic, pot-type core-half 20. The core-half 20 preferably has a right circular cylindrical shape because a hole having a complementary shape can be readily cut with a circular trephine into the bone in which the internal core assembly 6 is to be inserted.

In addition to the first member 4, the present invention includes a second member 22 which in the preferred embodiment includes signal generating and transmitting means 24 located supercutaneously of the user of the invention. FIG. 1 reveals the means 24 includes a sound detector and signal conditioner means 26 and an external coil assembly 28.

The external coil assembly 28 includes a second electrically conductive coil 29. In the preferred embodiment the second coil 29 includes four hundred turns of 38 AWG copper wire wound on a second support member comprising a delrin bobbin and a ceramic, pot-type core-half similar to the bobbin 18 and core-half 20 shown in FIG. 2 constituting the internal coil assembly 6.

The sound detector and signal conditioner 26 is electrically connected to the second electrically conductive coil 29 and generates an electrical signal which is electromagnetically transferred transcutaneously by the second coil 29 to the first coil 10 for electrically stimulating the subcutaneous tissue (specifically, the cochlea) in which the electrodes 12 and 14 of the first coil 10 are embedded. FIG. 4 shows the sound detector and signal conditioner means 26 includes a transducer, specifically a microphone 30, for detecting a sound and converting it into a proportional electrical signal. The proportional electrical signal is amplified by amplifier means 32 and input into amplitude modulation circuit means 34. The amplitude modulation circuit means 34 utilizes the amplified electrical signal to modulate a carrier signal which is generated by carrier frequency generator means 36. In the preferred embodiment the carrier frequency generator means 36 provides a 16 kHz carrier signal which is amplitude modulated by the electrical signal coming from the amplifier means 32. The resultant amplitude modulated signal is provided to the second coil 29 for electromagnetic transmission transcutaneously through the intervening tissue 8 to the first coil 10. The microphone 30, amplifier means 32, amplitude modulation circuit means 34 and carrier frequency generator means 36 depicted in FIG. 4 are of the type as are known in the art.

For the electromagnetically inductive transmission between the first coil 10 and the second coil 29 to be properly achieved, it is necessary to provide means for properly securing the external coil assembly 28 (and the sound detector and signal conditioner means 26 if it is unistructurally combined with the external coil assembly 28) with the internal assembly 6 without significantly adversely affecting the intervening tissue 8. This is achieved in the present invention with magnet means for magnetically securing the second member 22 with the first member 4. The magnet means electromagnetically associates the receiver means provided by the preferred embodiment internal coil assembly 6 with the transmitter means provided by the preferred embodiment means 24 so that the first coil 10 of the receiver means is responsive to the transmitted electrical signal transmitted by the second coil 29 of the preferred embodiment transmitter means.

In the preferred embodiment receiver means or internal coil assembly 6 shown in FIG. 2 the magnet means includes a rare-earth element which is particularly a first rare-earth magnet 38 associated with the first coil 10 by being concentrically positioned therewith in the pot-type core-half 20. The rare-earth element included within the magnet means may be any appropriate one of the group of chemical elements including atomic numbers between 58 and 71. In the preferred embodiment the rare-earth element is samarium which is combined with cobalt to provide a samarium-cobalt magnet (e.g., $SmCo_5$) having a long magnetic stability and a large maximum energy product.

In addition to the first rare-earth magnet 38 forming a part of the magnet means of the present invention, there is a second rare-earth magnet associated with the second coil 29 of the second member 22 for magnetically coupling with the first rare-earth magnet 38 so that the first and second coils 10 and 29 are positioned for electromagnetically inductive coupling. The magnetic coupling arises by placing attractive poles of the first and second magnets toward each other so that the magnetic lines of force extend through the intervening tissue 8 to retain the internal and external coil assemblies in alignment adjacent the intervening skin. For example, the magnetic north pole of the first rare-earth magnet 38 can be positioned within the first member 4 (specifically, within the core-half 20) so that it lies closer to the second member 22 (specifically, the core-half of the external coil assembly 28) than does the magnetic south pole of the first magnet 38. This positioning of the first magnet 38 requires that the magnetic south pole of the second rare-earth magnet be positioned in the second member 22 so that it will magnetically couple with the magnetic north pole of the first magnet when the second member 22 is placed to properly position the second coil 29 relative to the first coil 10.

To use the preferred embodiment of the present invention depicted in FIGS. 1-4, the first member 4 containing the first rare-earth magnet 38 is subcutaneously implanted in the user of the apparatus. During implantation the electrodes 12 and 14 of the first coil 10 are implanted in the respective locations previously described. Next, the second member 22, having the second rare-earth magnet associated therewith, is positioned supercutaneously adjacent the outer surface of the user's skin so that the first and second magnets magnetically secure themselves together thereby properly positioning the first and second coils 10 and 29 for maximum signal transference from the second member 22 to the first member 4.

The signal which is to be transferred from the second member 22 to the first member 4 is obtained by using the transducer or microphone 30 to detect an ambient sound and converting it into a proportional electrical signal, amplifying this signal, and amplitude modulating with this amplified signal the 16 kHz carrier signal generated by the carrier frequency generator means 36. The amplitude modulated signal is transferred to the second coil 29 of the second member 22 for electromagnetically inductive coupling with the first coil 10 of the first member 4. The electromagnetically induced signal received by the first coil 10 is impressed across the reference tissue and cochlea tissue to which the electrodes of the first coil are embedded. This electrical stimulation of the cochlea enhances the hearing and lip-reading skills of the user.

The previously described type of system utilizing the single first coil 10 and the single second coil 29 is known as a single-channel hearing aid because only a single signal is transferred to the user of the apparatus at any one time. However, there are multi-channel devices which are being developed for simultaneously transferring a plurality of signals to permit frequency coding and subsequent frequency anaylsis of the detected sounds. To insure the proper operation of such multi-channel devices, it is necessary to accurately align the respective transmitting and receiving channels comprising, for example, a plurality of coils similar to those shown in the drawings. The initial alignment and subsequent maintenance of the alignment would be difficult using the preferred embodiment shown in FIGS. 1-4 because with only a single pair of magnets, the first member and second members could rotate whereby respective channels could become misaligned. To prevent misalignment, a plurality of magnets forming a multiple number of magnet pairs can be used as shown in a second preferred embodiment illustrated in FIG. 5. It is to be noted that although the FIG. 5 embodiment is of the single-channel type, it could readily be adapted to a multi-channel type.

The FIG. 5 embodiment discloses a support member 40 and coil assembly 42 similar to that shown in FIGS. 2 and 3. However, the magnet means of the FIG. 5 embodiment is different from that shown in FIG. 2 because two rare-earth magnets are disposed in the support member 40 of FIG. 5. A first rare-earth magnet 44 is magnetically coupled with a second rare-earth magnet (not shown) which is properly situated in a second member which is similar to the second member 22. A third rare-earth magnet 46 shown in FIG. 5 is paired with a fourth rare-earth magnet (not shown) which is properly situated in the second member of the second preferred embodiment. Therefore, the magnets are grouped in attractive magnetic relation between the receiver and transmitter means of the first and second members, respectively.

It is apparent that through the use of the plurality of magnets depicted in FIG. 5, misalignment is less likely to occur once the first and second members are magnetically coupled. However, it is sometimes necessary to orient the first member with respect to the second member in a single, predetermined alignment.

If the two magnets of the first member shown in FIG. 5 had the same polarity orientation and the two magnets of the second member had the same polarity orientation as between themselves but opposite that of the magnets of the first member, the second member could be magnetically coupled to the first member in either of two directions. For example, if each of the magnets 44 and 46 shown in FIG. 5 had its magnetic north pole facing the second member and each of the magnets in the second member had its magnetic south pole facing the first member, the first and second members could be positively related so that either the first and second magnets and the third and fourth magnets were magnetically coupled or the first and fourth magnets and the second and third magnets were magnetically coupled.

To restrict the alignment between the first and second members to a single predetermined position, the first and third rare-earth magnets 44 and 46 can be disposed in the first member so that the two polarities facing the second member are opposite. For example, the first magnet could have its magnetic north pole disposed for coupling with the second member and the third magnet could have its magnetic south pole disposed for coupling with the second member. To complement this pole placement, the second magnet could be disposed in the second member so that its magnetic south pole is disposed for coupling with the first member and the third magnet could be disposed in the second member so that its magnetic north pole is disposed for coupling with the first member. With such magnetic polarities positioned for coupling the first and second members, the first and second members can only be magnetically coupled in a single alignment because coupling will occur only when the first magnet and second magnet are aligned and the third magnet and fourth magnet are aligned. The reverse alignment of the magnets of the first and second members results in similar poles facing each other thereby causing a repulsive force. This can be more generally stated by saying that the third and fourth magnets have as their attractive polarities magnetic poles of opposite polarities to the attractive polarities of the first and second magnets, respectively.

Although the specific embodiments described above disclose either a single pair of magnetic slugs in the shape of small disks located in the centers of symmetrical pot-type core halves or two such pairs of magnetic slugs, it is to be noted that other configurations are also feasible. For example, a ring magnet disposed along the periphery of the pot-type core-half could be used. Likewise, three disk-shaped magnets could be spaced at 120° intervals around each of the first and second members. Still further, a single magnet could be disposed in either the internal member or the external member and a magnetically attractive material, such as a ferromagnetic material, could be placed in the other member so that the attractive material is held in alignment by the single magnet. Other forms of magnet means can likewise be used and yet remain within the scope of the present invention.

It is also to be noted that although the preferred embodiment of the present invention was described with reference to a bio-electronic signal coupling device (more particularly, a hearing aid), the present invention contemplates any medical apparatus having a first member implanted below the surface of the skin of the user and having a second member located externally to the user's skin but transcutaneously coupled to the first member.

Still further, it is to be noted that the term "hearing aid" as used herein is not limited to those devices which amplify sounds, but rather is intended to encompass all suitable devices which assist one in hearing and/or comprehending sound.

Thus, the present invention of a medical apparatus coupling device is well adapted to carry out the objects and attain the ends and advantages mentioned above as well as those inherent therein. While preferred embodiments of the invention have been described for the purpose of this disclosure, numerous changes in the construction and arrangement of parts can be made by those skilled in the art, which changes are encompassed within the spirit of this invention as defined by the appended claims.

What is claimed is:

1. A transcutaneous coupling apparatus, comprising:
   a first member positioned subcutaneously;
   a second member positioned supercutaneously; and
   magnet means for magnetically securing said second member to said first member.

2. An apparatus as defined in claim 1, wherein said magnet means includes a rare-earth element.

3. An apparatus as defined in claim 1, wherein:
   said first member includes electronic means for receiving an electrical signal; and
   said second member includes electronic means for transmitting the electrical signal.

4. An apparatus as defined in claim 3, wherein said magnet means includes a rare-earth element.

5. An apparatus as defined in claim 1, wherein:
   said first member includes electronic means for transmitting an electrical signal; and
   said second member includes electronic means for receiving the electrical signal.

6. An apparatus as defined in claim 5, wherein said magnet means includes a rare-earth element.

7. An apparatus as defined in claim 1, wherein:
   said transcutaneous coupling apparatus is a bio-electronic signal coupling device;
   said first member includes:
      a first electrically conductive coil having two ends, each of said two ends being embedded in subcutaneous tissue; and
   said second member includes:
      a second electrically conductive coil; and
      signal generating means, electrically connected to said second coil, for providing an electrical signal to said second coil so that said signal is electromagnetically transferred transcutaneously to said first coil for electrically stimulating the subcutaneous tissue.

8. An apparatus as defined in claim 7, wherein said magnet means includes a rare-earth element.

9. An apparatus as defined in claim 7, wherein said magnet means includes:
   a first rare-earth magnet associated with said first coil; and
   a second rare-earth magnet, associated with said second coil, for magnetically coupling with said first rare-earth magnet so that said first and second coils are positioned to achieve electromagnetically inductive coupling.

10. An apparatus as defined in claim 9, wherein said magnet means further includes:
    a third rare-earth magnet associated with said first coil; and
    a fourth rare-earth magnet, associated with said second coil, for magnetically coupling with said third rare-earth magnet, said third and fourth magnets having as their attractive polarities magnetic poles of opposite polarities to the attractive polarities of said first and second magnets, respectively.

11. A hearing air, comprising:
    sound detector means for detecting sound and converting it into an electrical signal;
    transmitter means, positioned on the outside of the skin of a user of said hearing aid, for transmitting the electrical signal;

receiver means, positioned beneath the skin of the user, for receiving the transmitted electrical signal; and magnet means for coupling said transmitter means with said receiver means so that said transmitter means and said receiver means are on opposite sides of the surface of the skin of the user.

12. A hearing aid as defined in claim 11, wherein said magnet means includes a rare-earth element.

13. A hearing aid as defined in claim 12, wherein:
said receiver means includes a first electrically conductive coil;
said transmitter means includes a second electrically conductive coil, said first and second coils being electromagnetically associated by said magnet means so that said first coil is responsive to the transmitted electrical signal.

14. A hearing aid as defined in claim 13, wherein said first coil includes an end embedded in a cochlea of the user.

15. A hearing aid as defined in claim 14, wherein said sound detector means includes:
transducer means for receiving a sound and converting it to a proportional electrical signal;
amplifier means for amplifying the proportional electrical signal;
carrier generator means for generating a carrier electrical signal; and
amplitude modulation means, responsive to said amplifier means, for modulating the amplitude of the carrier electrical signal and for transferring the modulated carrier electrical signal to said second coil.

16. A hearing aid as defined in claim 15, wherein:
said receiver means further includes a first support member having said first coil associated therewith;
said transmitter means further includes a second support member having said second coil associated therewith; and
said magnet means includes:
  a first rare-earth magnet associated with said first support member so that a first polarity of said first magnet is positioned closer to said transmitter means than is a second polarity thereof; and
  a second rare-earth magnet associated with said second support member so that a polarity thereof attractive to the first polarity of said first rare-earth magnet is positioned closer to said first magnet than is a non-attractive polarity thereof.

17. A hearing aid as defined in claim 11, wherein said magnet means includes a plurality of rare-earth magnets, each of said magnets being associated with a respective one of said transmitter means and said receiver means and being grouped in attractive magnetic relation with another one of said magnets associated with the other of said transmitter means and said receiver means so that said transmitter means and said receiver means are magnetically coupled in a predetermined alignment.

18. A hearing aid, comprising:
sound detector means for detecting sound and for converting it into an electrical signal;
a first electrically conductive coil having a first end embedded in the body tissue of a user of said hearing aid and having a second end embedded in a cochlea of the user;
a second electrically conductive coil connected to said sound detector means and positioned outside the skin of the user;
a first rare-earth magnet associated with said first coil; and
a second rare-earth magnet, associated with said second coil, for magnetically coupling with said first rare-earth magnet so that said first and second coils are positioned to achieve electromagnetically inductive coupling.

19. A hearing aid as defined in claim 18, further comprising:
a third rare-earth magnet associated with said first coil; and
a fourth rare-earth magnet, associated with said second coil, for magnetically coupling with said third rare-earth magnet, said third and fourth magnets having as their attractive polarities magnetic poles of opposite polarities to the attractive polarities of said first and second magnets, respectively.

20. A method of transcutaneously coupling an apparatus having an implantable member and an external member, comprising the steps of:
associating a first rare-earth magnet with the implantable member;
associating a second rare-earth magnet with the external member;
subcutaneously implanting the implantable member with the associated first rare-earth magnet; and
supercutaneously positioning the external member and associated second rare-earth magnet so that the second rare-earth magnet is magnetically secured with the first rare-earth magnet.

21. A method as defined in claim 20, further comprising the steps of:
associating, prior to the step of subcutaneously implanting the implantable member, a third rare-earth magnet with the implantable member in opposing magnetic polarity relation with the first rare-earth magnet; and
associating a fourth rare-earth magnet with the external member in opposing magnetic polarity relation with the second rare-earth magnet so that the fourth rare-earth magnet is magnetically secured with the third rare-earth magnet during the step of supercutaneously positioning the external member and so that the external member and the implanted member are coupled in a predetermined relation.

* * * * *

UNITED STATES PATENT AND TRADEMARK OFFICE
CERTIFICATE OF CORRECTION

PATENT NO. : 4,352,960

DATED : October 5, 1982

INVENTOR(S) : Kenneth J. Dormer et al.

It is certified that error appears in the above-identified patent and that said Letters Patent is hereby corrected as shown below:

Column 8, line 63, Claim 11, line 1, "air" should read -- aid --.

Signed and Sealed this

Fifteenth Day of March 1983

[SEAL]

Attest:

Attesting Officer

GERALD J. MOSSINGHOFF

Commissioner of Patents and Trademarks